United States Patent [19]

St. Pierre et al.

[11] Patent Number: 5,427,777

[45] Date of Patent: Jun. 27, 1995

[54] INGESTIBLE POLYMERIC PHOSPHONIUM SALTS, COMPOSITION THEREOF AND METHOD OF TREATING HYPERCHOLESTEROLEMIA

[75] Inventors: Leon E. St. Pierre, Frelighsburg; George R. Brown, Dollard-Des-Ormeaux; Zhanjie Tan, Toronto; Sophie-Dorothee Clas, Town of Mount Royal, all of Canada

[73] Assignee: Lowchol Scientific, Inc., Frelighsburg, Canada

[21] Appl. No.: 856,184

[22] Filed: Mar. 23, 1992

[51] Int. Cl.$^6$ ............ A61K 31/74; A61K 31/80
[52] U.S. Cl. ................ 424/78.01; 424/78.1; 521/38; 526/277
[58] Field of Search ............ 424/78.1, 78.01; 521/31, 38, 30; 526/277; 514/821

[56] References Cited

U.S. PATENT DOCUMENTS

| | | | |
|---|---|---|---|
| 2,781,290 | 2/1957 | Martin et al. | 424/78.1 |
| 4,446,284 | 5/1984 | Parker | 525/383 |
| 4,774,262 | 9/1988 | Blanquet et al. | 521/25 |
| 4,775,651 | 10/1988 | Tachikawa et al. | 521/31 |
| 4,996,047 | 2/1991 | Kelleher et al. | 424/78.1 |
| 5,114,709 | 5/1992 | St. Pierre et al. | 424/78.12 |

FOREIGN PATENT DOCUMENTS 934285 8/1963 United Kingdom ........... 424/78.14

*Primary Examiner*—D. Gabrielle Phelan
*Assistant Examiner*—Peter F. Kulkosky
*Attorney, Agent, or Firm*—Phillips Moore Lempio & Finley

[57] ABSTRACT

Novel ingestible polymeric phosphonium salts have the formula:

$$P'-[(CH_2)_{n_1}P^+(R)_2]_{m_1}[(CH_2)_{n_2}P^+(R)_2]_{m_2}R \cdot (m_1+m_2)X^- \quad (Ia)$$

$$P'-(CH_2)_n- \quad (Ib)$$

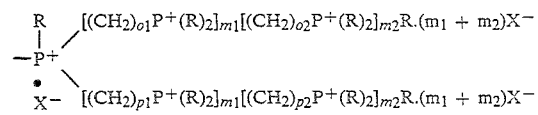

or $$P'-(CH_2)_n- \quad (Ic)$$

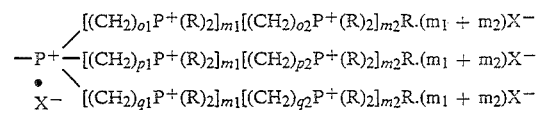

wherein P' represents a cross-linked and non-digestible polymer backbone; R is a lower alkyl radical; $X^-$ is a pharmaceutically acceptable anion; n, $n_1$ and $n_2$ are, independently, integers varying from 0 to 6 inclusive, with the proviso that when $m_1 \geq 1$, $n_2 \geq 1$; and $o_1$, $o_2$, $p_1$, $p_2$, $q_1$ and $q_2$ are, independently, integers varying from 1 to 6 inclusive. The polymeric phosphonium salts of the invention are highly efficient sorbents for bile acids and salts and can thus be used for reducing hypercholesterolemia in affected humans.

17 Claims, 2 Drawing Sheets

INGESTIBLE POLYMERIC PHOSPHONIUM SALTS, COMPOSITION THEREOF AND METHOD OF TREATING HYPERCHOLESTEROLEMIA

BACKGROUND OF THE INVENTION

1. Field of the Invention

The present invention relates to novel ingestible polymeric phosphonium salts which are useful as sorbents for bile salts. More particularly, the invention is directed toward the treatment of hypercholesterolemia by removing through sorption the bile acids and salts from the small intestine, thereby increasing the catabolism of cholesterol in the liver with a concomitant decrease in the blood cholesterol level.

2. Description of the Background

All available evidence indicates that the incidence of higher than normal blood serum cholesterol levels in humans is associated with atherosclerosis and other hypercholesterolemic disease signs. Hypercholesterolemia, the leading cause of death in many countries, is presently treated by restricted and special dietary intake, inhibition of cholesterol synthesis, accelerated catabolism and prevention of gastrointestinal adsorption, i.e., interruption of enterohepatic circulation. Increased catabolism of cholesterol can be achieved by the oral administration of bile salt binding agents.

Cholestyramine, the most widely used adsorbent for bile salts, is a copolymer of polystyrene and divinylbenzene with quaternary ammonium groups as functional groups. Being a typical strongly basic ion exchanger, its counterions of the quaternary ammonium, usually chloride ions, are exchanged with bile salt anions during the binding. The hydrophobic nature of the polymer backbone results in its poor biocompatibility. As a consequence, adverse side effects have been experienced by hypercholesterolemic patients. The drug has to be taken in large dosage and may cause stomach discomfort to patients.

Although widely used, non-absorbable sorbents such as the positively charged amine containing materials sold under the trade marks QUESTRAN and COLESTID have the setbacks of low adsorption capacity and undesirable side effects and are not completely satisfactory. Since hypercholesterolemia is a well recognized cause of cardiovascular disease, new and better drugs are urgently needed to replace the existing materials.

It is therefore an object of the present invention to overcome the above drawbacks and to provide novel bile salt sorbents with high sorption capacities, specificity and biocompatibility.

SUMMARY OF THE INVENTION

In accordance with the invention, there is provided a pharmaceutically acceptable, linear or branched polymeric phosphonium salt having the chemical formula:

$$P'-[(CH_2)_{n_1}P^+(R)_2]_{m_1}[(CH_2)_{n_2}P^+(R)_2]_{m_2}R.(m_1+m_2)X^- \quad (Ia)$$

$$P'-(CH_2)_n- \quad (Ib)$$

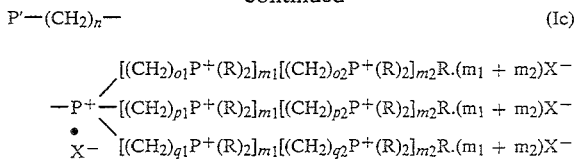

or

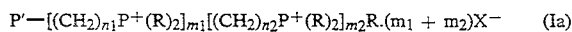
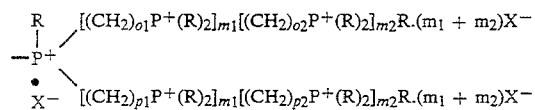

wherein
- P' represents a cross-linked and non-digestible polymer backbone;
- R is a lower alkyl radical;
- $X^-$ is a pharmaceutically acceptable anion;
- $m_1$ and $m_2$ are, independently, integers varying from 0 to 5 inclusive, with the proviso that $m_1+m_2 \geq 1$;
- n, $n_1$ and $n_2$ are, independently, integers varying from 0 to 6 inclusive, with the proviso that when $m_1 \geq 1$, $n_2 \geq 1$; and
- $o_1$, $o_2$, $p_1$ $p_2$, $q_1$ and $q_2$ are, independently, integers varying from 1 to 6 inclusive.

Other objects, advantages and features of the present invention will become apparent to those skilled in the art from the following discussion.

DESCRIPTION OF THE PREFERRED EMBODIMENTS

It has been found quite unexpectedly that the above polymeric phosphonium salts are highly efficient sorbents for cholic acid and glycocholic acid as well as other bile acids, such as chenodeoxycholic acid, lithocholic acid, deoxycholic acid and taurocholic acid. The significance of the bile acid sorption is related to the lowering of serum cholesterol. As it is known, cholesterol is a major and probably the sole precursor of bile acids during normal digestion, bile acids are secreted via the bile from the liver and the gallbladder into the intestine. Bile acids emulsify the fat and lipid materials present in the foods, thus facilitating adsorption. A major portion of bile acids secreted is reabsorbed from the intestines and returned via the portal circulation of the liver, thus completing the enterohepatic cycle. The binding of bile acids in the intestines onto an insoluble sorbent that is excreted in the feces results in partial removal of bile acids from the enterohepatic circulation, preventing their readsorption. The increased fecal loss of bile acids leads to an increased oxidation of cholesterol to bile acids, a decrease in beta lipoprotein or low density lipoprotein serum levels, and a decrease in serum cholesterol level. Thus, the compounds of the invention can be used for reducing hypercholesterolemia in affected humans.

In one preferred embodiment, the compound of formula (Ia) of this invention is one, wherein $m_1+m_2>1$. This case is represented in the exemplary disclosure.

In another embodiment, the phosphonium salt of the invention is one wherein P' represents a hydrophobic, cross-linked and non-digestible polymer backbone. In still other preferred embodiments the P' backbone represents a poly(p-methylene styrene) backbone or a poly (p-aminomethyl styrene) backbone.

In still another preferred embodiment, the phosphonium salt of the formula (Ia) is one wherein R is methyl, ethyl or butyl; $n_1$ is 1; $m_2$ is 1; $n_1$ is 0 or 2, and $n_2$ is 2; P' represents a poly(p-methyl styrene) or poly(p-aminomethyl styrene) backbone; and $X^-$ is a pharmaceutically-acceptable anion.

In still another preferred embodiment, the phosphonium salt of the invention is one wherein R is methyl; $m_1$ are $m_2$ are each 1; $n_1$ is 0, and $n_2$ is 2; P' represents a poly(p-methylene styrene) backbone; and $X^-$ is a pharmaceutically-acceptable anion.

One of the most preferred embodiments is a phosphonium salt of the invention of formula (Ib) or (Ic), wherein R is methyl; $m_1$ and $m_2$ are each 1; n, $o_1$, $o_2$, $p_1$, $p_2$, $q_1$ and $q_2$ are each 2; P' represents a poly(p-methylene styrene) or poly(p-aminomethyl styrene) backbone; and $X^-$ is a pharmaceutically-acceptable anion.

Accordingly, the present invention also provides, in a further aspect thereof, a method of treating hypercholesterolemia in an affected human, which comprises administering to the affected human an effective amount of a bile salt adsorbent consisting of polymeric phosphonium salt as defined above.

According to yet another aspect of the invention, there is provided a pharmaceutical composition for the treatment of hypercholesterolemia, which comprises as active ingredient a polymeric phosphonium salt as defined above, together with a pharmaceutically acceptable carrier thereof.

The polymer backbone to which the phosphonium groups are chemically bonded must be cross-linked to prevent the sorbent from diffusing from the digestive tract, as well as non-digestible to prevent the sorbent from being broken down and absorbed into the body. A preferred hydrophilic polymer resin for use as backbone in the phosphonium salts of formulas (Ia), (Ib) or (Ic) is a porous, cross-linked poly(methyl acrylate) resin; such a resin is advantageously prepared by polymerizing methyl acrylate in the presence of two cross-linking agents used in a ratio of 1:1. The porosity of the resin permits diffusion of the bile salts which are to be sequestered, thereby improving adsorption capacity. A cross-linked poly(glycidyl methacrylate) resin can also be used as hydrophilic backbone. A preferred hydrophobic polymer resin for use as backbone in the phosphonium salts of the invention is a cross-liked poly(p-chloromethyl styrene) resin. Such a resin is sold under the trade mark BIO-BEADS S-X1 by Bio-Rad Laboratories.

Particularly, preferred phosphonium salts according to the invention are the linear polymers of formula (Ia) in which R is a methyl, ethyl or butyl radical, $m_1$ is 1, $m_2$ is 0 or 1, $n_1$ is 0 or 2, $n_2$ is 2, P' represents a poly(p-methylene styrene) or poly(p-aminomethyl styrene) backbone and $X^-$ is a pharmaceutically acceptable anion such as $Cl^-$, $I^-$ or $OH^-$.

Amongst the branched phosphonium salts of formula (Ib) or (Ic), the preferred compounds are those in which R is a methyl radical, $m_1$ and $m_2$ are each 1, n, $o_1$, $o_2$, $p_1$ and $p_2$ are each 2, P' represents a poly(p-methylene styrene) or poly(p-aminomethyl styrene) backbone and $X^-$ is a pharmaceutically acceptable anion.

The polymeric phosphonium salts according to the invention not only exhibit high sorption capacity but also high water-swellability, which render them suitable for clinical application.

Further features and advantages of the invention will become more readily apparent from the following non-limiting examples and the accompanying drawings, in which:

Having now generally described this invention, the same will be better understood by reference to certain specific examples, which are included herein for purposes of illustration only and are not intended to be limiting of the invention or any embodiment thereof, unless so specified.

EXAMPLES

Example 1: Preparation of Samples

Tris(hydroxymethyl)-aminomethane (Aldrich) and 1,000 N standard HCl solution were used to prepare buffered solutions with ionic strength 0.0025 M (pH=7.01) and 0.005 M (pH=7.01). With these buffers, a bile salt solution with a concentration of about 50 mg/dl was prepared and used directly. Into bottles of different sizes (2–100 ml), about 5–15 mg of the phosphonium salt to be tested was weighed. Then different volumes of bile salt solution (1–50 ml) were added into the bottles. By changing the volumes of the bile salt solution added, a whole range of bile salt equilibrium concentrations was easily reached. Alternatively, fixed volumes of solutions initially having different acid concentrations were also used. They were shaken at room temperature (15°–25°) for more than 2 hours. Then they were filtered and the clear solutions were analyzed by High Performance Liquid Chromatography (HPLC).

Example 2: Preparation of Phosphonium Salt I 7.9 grams of dry BIO-BEADS S-X1, a cross-linked poly(p-chloromethylene styrene) resin and 150 ml of dichloromethane were mixed in a 3-necked flask equipped with a mechanical stirrer. 25 grams of trimethylphosphine were cooled, transferred to the reaction flask and stirring was continued for 8 days at room temperature. The mixture was filtered, washed several times with dichloromethane, water, methanol, and finally with anhydrous diethyl ether. The product obtained was then dried under vacuum at room temperature for several days.

The functionality of this material, designated "phosphonium salt I", was determined by potentiometric titration with $AgNO_3$ to be 3.0±0.1 mmol chloride/g salt (95% yield). New peaks at 965 (P—$CH_3$ rocking), 1299 (P—$CH_3$ symmetric deformation), and 1420 cm$^{-1}$ ($CH_2$ deformations in P—$CH_3$ were obtained by FT-IR on KBr disks. The peak due to chloromethylated styrene, at 1265 cm$^{-1}$, had essentially completely disappeared.

Figure 1:
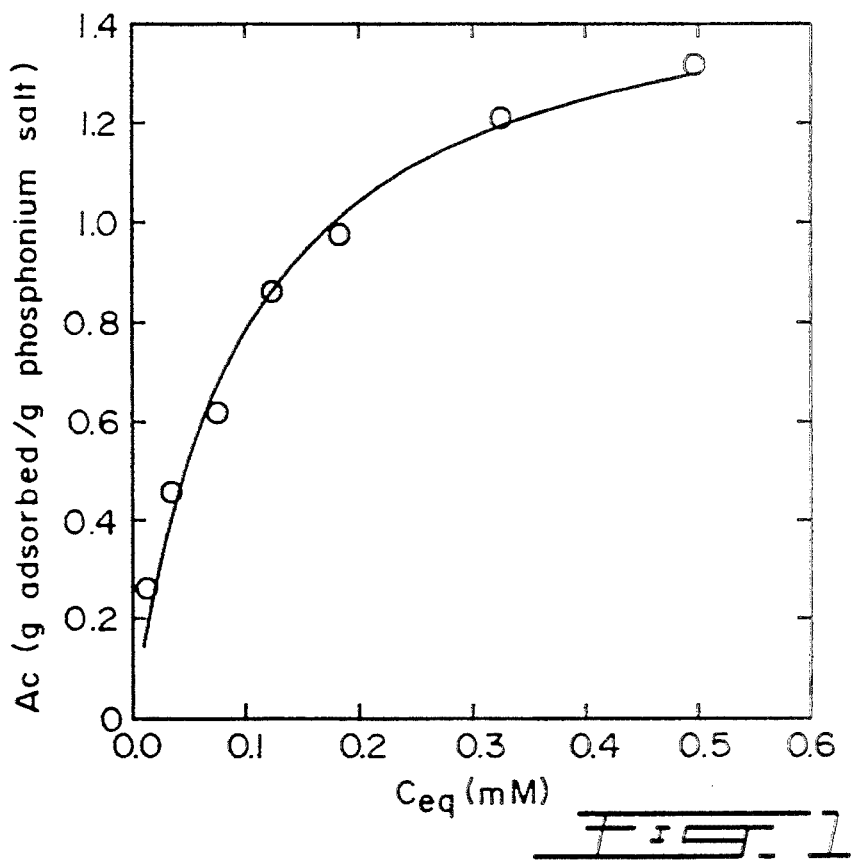
FIGS. 1 and 2 show the sorption isotherms of compounds according to the invention for sodium glycocholate in 0.0025 M, pH= 7.01 Tris-HCl buffer.

The phosphonium salt was stirred with a $Na^+$-glycocholate solution in Tris-HCl buffer at an initial bile salt concentration of 40–60 mg/dl at room temperature, for more than 2 hours. The amount of $Na^+$-glycocholate sorbed was measured by HPLC as described above. The sorption isotherm is shown in FIG. 1. At an equilibrium concentration of 0.5 mM, this phosphonium salt sorbed 1.27 gram of $Na^+$-glycocholate per gram of phosphonium salt.

Example 3: Preparation of Phosphonium Salt II 0.32 gram of dry BIO-BEADS SX-1 and 2 ml of 1,2-bis(dimethylphosphino)ethane were mixed in a 5 ml round bottom flask. The flask was stoppered and shaken on a wrist-action mechanical shaker at room temperature (24.9° C.) for 43.5 hours. The mixture was filtered, washed several times with acetonitrile and anhydrous diethyl ether, and finally dried on the funnel for 30 minutes.

Quaternization was carried out by transferring the diphosphonium-containing resin thus obtained to a 5 ml round bottom flask to which was added neat methyl iodide. The reaction flask was shaken in the absence of light for 12 days at room temperature. A yellow powder was collected and washed with methanol and anhydrous diethyl ether. It was then dried under vacuum at room temperature for several days.

The quaternized resin (in the iodide form) was then converted to its chloride form with saturated (4.5 M) NaCl solution. It was shaken in the salt solution for 2 days, filtered and washed with more NaCl solution. Washing was continued until no yellow precipitate (due to the iodide) was obtained in the filtrate with $AgNO_3$. It was then washed with water until no precipitate was obtained in the filtrate with $AgNO_3$ (ensuring removal of excess chloride), followed by methanol and finally with anhydrous diethyl ether. The yellow powder was dried under vacuum at room temperature for several days.

The functionality of this material, designated "phosphonium salt II", was determined by potentiometric titration in $KNO_3$ with $AgNO_3$ to be 4.05 mmol chloride/g salt (90% yield). KBr-FT-IR of the salt yielded new peaks at 1451 and 1418 $cm^{-1}$ ($CH_2$ rocking in P—$CH_2$), 1302 $cm^{-1}$ (P—$CH_3$ symmetric deformation) and 962 $cm^{-1}$ (P—$CH_3$ rocking). There was essentially no peak at 1265 $cm^{-1}$ (present in chloromethylated styrene).

Figure 2:
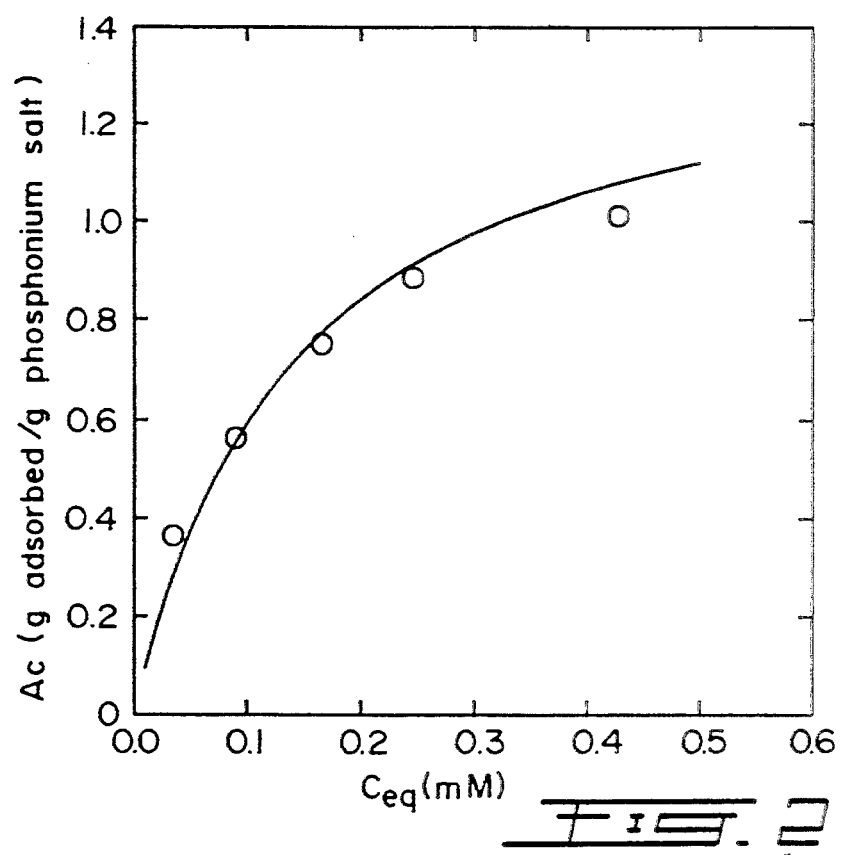

The phosphonium salt sorbed 1.10 gram of $Na^+$-glycocholate per gram of phosphonium salt at an equilibrium concentration of 0.5 mM. The sorption isotherm is shown in FIG. 2.

Example 4: Preparation of Phosphonium Salt III 4.0 grams of BIO-BEADS SX-1 were swollen in 40 ml of dimethylformamide and 6.0 ml of triethylphosphine were added at 60° C. under stirring and $N_2$ protection. Then, the temperature was gradually increased to 80° C. and maintained at 80° C. for 48 hours. The product obtained was filtered and washed successively with ethanol, water and ethanol. It was extracted with ethanol for two days and dried under vacuum at 60° C.

Figure 3:
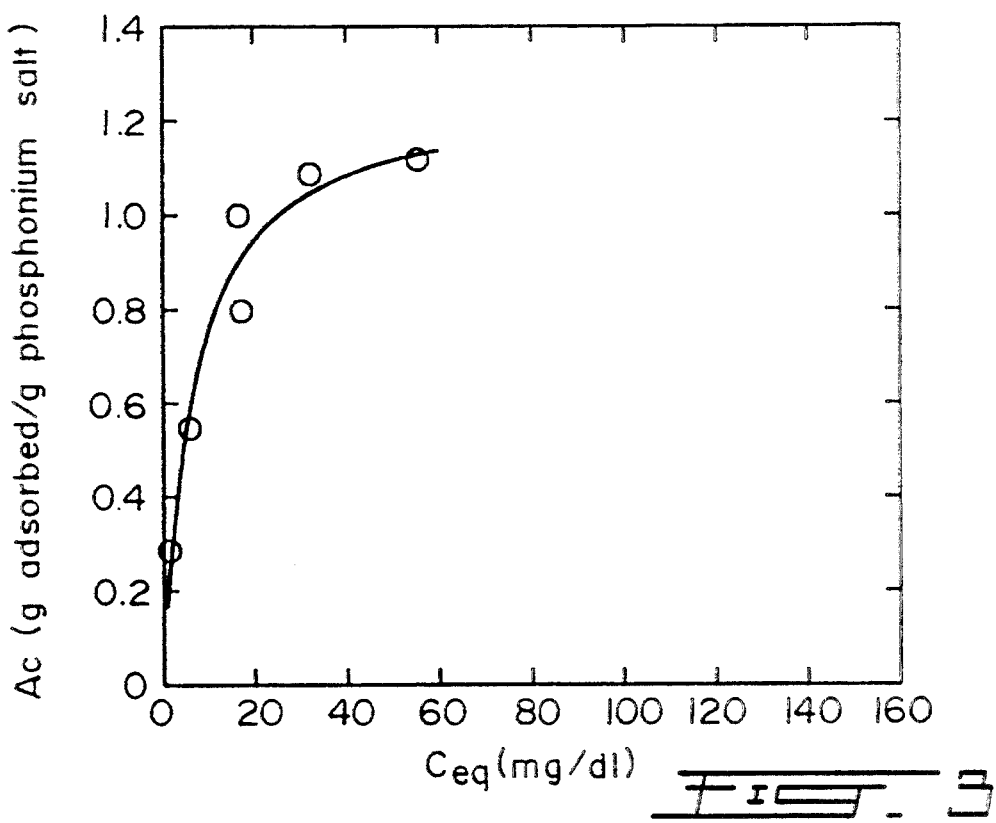
FIGS. 3 and 4 show the sorption isotherms of other compounds according to the invention for sodium glycocholate in 0.005 M, pH= 7.01 Tris-HCl buffer.

This material, designated "phosphonium salt III", sorbed 1.14 gram of $Na^+$-glycocholate per gram of phosphonium salt at an equilibrium concentration of 50 mg/dl. The sorption isotherm is shown in FIG. 3.

Example 5: Preparation of Phosphonium Salt IV 4.0 grams of BIO-BEADS SX-1 were swollen in 40 ml of 1,2-dichloroethane. 4.0 grams of 2-chloroethylamine monochloride dissolved in 4 ml of water were added, followed by the addition of 10 ml 20% NaOH solution over a period of 6 hours at 60° C. The reaction temperature was maintained for another two hours. The 2-chloroethylamine anchored poly(pchloromethyl styrene) resin thus obtained was filtered and washed successively with ethanol, water and ethanol.

0.4 gram of the 2-chloroethylamine anchored poly(p-chloromethyl styrene) resin were swollen in 3 ml of dimethylformamide and 3 ml of tributylphosphine were added at 60° C. under stirring and $N_2$ protection. Then, the temperature was gradually increased to 80° C. and maintained at 80° C. for three days. The product obtained was filtered and washed successively with ethanol, water and ethanol. It was extracted with ethanol for two days and dried under vacuum at 60° C.

Figure 4:
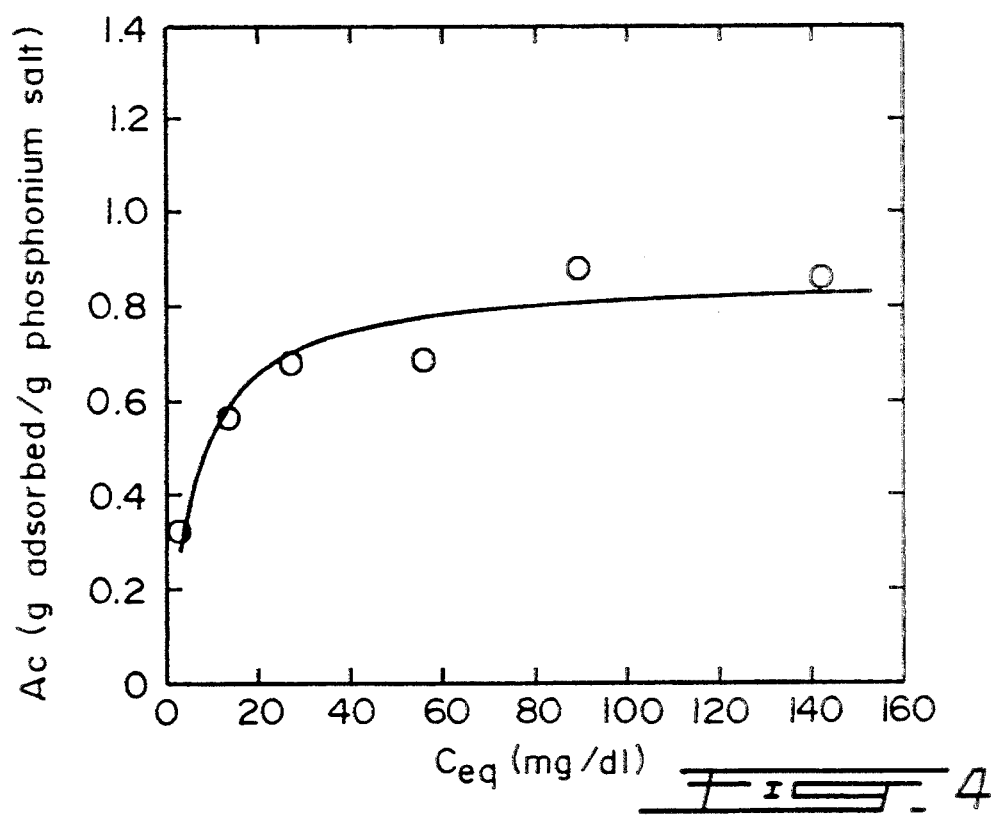

This material, designated "phosphonium salt IV", sorbed 0.80 gram of $Na^+$-glycocholate per gram of phosphonium salt at an equilibrium concentration of 80 mg/dl. The sorption isotherm is shown in FIG. 4.

The sorption capacities of the polymeric phosphonium salts prepared in Examples 1 through 4 are summarized in the following Table.

TABLE

| Ex. No. | Product Designation | Structure of Phosphonium Salt | Sorption Capacity (*) |
| --- | --- | --- | --- |
| 2 | Phosphonium Salt I | $P_1$—$[P^+(CH_3)_2]CH_3.Cl^-$ | 1.27 |
| 3 | Phosphonium Salt II | $P_1$—$[P^+(CH_3)_2][(CH_2)_2P^+(CH_3)_2]CH_3.2Cl^-$ | 1.10 |
| 4 | Phosphonium Salt III | $P_1$—$[P^+(C_2H_5)_2]C_2H_5.Cl^-$ | 1.14 |
| 5 | Phosphonium Salt IV | $P_2$—$[(CH_2)_2P^+(C_4H_9)_2]C_4H_9.Cl^-$ | 0.80 |

The invention now being fully described, it will be apparent to one of ordinaty skill in the art that many changes and modifications can be made thereto without departing from thee spirit or scope of the invention as set forth herein.
$P_1$ = poly(p-methylene styrene) backbone
$P_2$ = poly(p-aminomethyl styrene) backbone
(*)gram of sodium glycocholate sorbed per gram of phosphonium salt The invention now being fully described, it will be apparent to one of ordinary skill in the art that many changes and modifications can be made thereto without departing from thee spirit or scope of the invention as set forth herein.

We claim:

1. A pharmaceutically-acceptable linear or branched polymeric phosphonium salt having a chemical formula selected from the group consisting of:

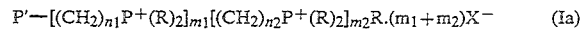

$$P'—[(CH_2)_{n1}P^+(R)_2]_{m1}[(CH_2)_{n2}P^+(R)_2]_{m2}R.(m_1+m_2)X^- \quad (Ia)$$

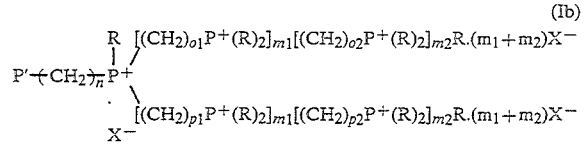

(Ib)

and

-continued $$P'\text{-}(CH_2)_n\overset{+}{P}\begin{matrix}[(CH_2)_{o1}P^+(R)_2]_{m1}[(CH_2)_{o2}P^+(R)_2]_{m2}R.(m_1+m_2)X^- \\ -(CH_2)_{p1}P^+(R)_2]_{m1}[(CH_2)_{p2}P^+(R)_2]_{m2}R.(m_1+m_2)X^- \\ [(CH_2)_{q1}P^+(R)_2]_{m1}[(CH_2)_{q2}P^+(R)_2]_{m2}R.(m_1+m_2)X^- \\ X^-\end{matrix} \quad (Ic)$$

wherein
P' represents a covalently cross-linked, non-digestible polymer backbone;
R is a lower alkyl radical;
$X^-$ is a pharmaceutically-acceptable anion;
$m_1$ and $m_2$ are each independently integers from 0 to 5 inclusive, with the proviso that in the chemical formula (Ia), $m_1+m_2>1$ and in chemical formulas (1 b) and (1 c), $m_1+m_2\geq 1$;
n, $n_1$ and $n_2$ are each independently integers from 0 to 6 inclusive, with the proviso that in the chemical formula (Ia) when $m_1\geq 1$, $n_2\geq 1$; and
$o_1$, $o_2$, $p_1$, $p_2$, $q_1$ and $q_2$ are each independently integers from 1 to 6, wherein said phosphonium salt has positively charged active sites effective for binding bile acid anions.

2. The polymeric phosphonium salt of claim 1, wherein P' represents a hydrophobic, covalently cross-linked, non-digestible polymer backbone.

3. The polymeric phosphonium salt of claim 1, wherein P' represents a poly(p-methylene styrene) backbone.

4. The polymeric phosphonium salt of claim 1, wherein P' represents a poly(p-aminomethyl styrene) backbone.

5. The polymeric phosphonium salt of chemical formula (Ia) of claim 1, wherein
R is methyl, ethyl or butyl;
$m_1$ is 1;
$m_2$ is 1;
$n_1$ is 0 or 2;
$n_2$ is 2; and
P' is selected from a poly(p-methylene styrene) or poly(p-aminomethyl styrene) backbone.

6. The polymeric phosphonium salt of claim 5, wherein
R is methyl;
$m_1$ and $m_2$ are each 1;
$n_1$ is 0;
$n_2$ is 2; and
P' is a poly(p-methylene styrene) backbone.

7. The polymeric phosphonium salt of formula (Ib) or (Ic) of claim 1 wherein
R is methyl;
$m_1$ and $m_2$ are each 1;
n, $o_1$, $o_2$, $p_1$, $p_2$, $q_1$ and $q_2$ are each 2; and
P' is selected from a poly(p-methylene styrene) or poly(p-aminomethyl styrene) backbone.

8. An anti-hyper-cholesterolemic pharmaceutical composition, which composition comprises:
as an active ingredient, a pharmaceutically-acceptable, linear or branched polymeric phosphonium salt having a chemical formula selected from the group consisting of:

$$P'\text{—}[(CH_2)_{n1}P^+(R)_2]_{m1}[(CH_2)_{n2}P^+(R)_2]_{m2}R.(m_1+m_2)X^- \quad (Ia)$$

-continued $$P'\text{-}(CH_2)_n\overset{+}{P}\begin{matrix}R \\ | \\ \end{matrix}\begin{matrix}[(CH_2)_{o1}P^+(R)_2]_{m1}[(CH_2)_{o2}P^+(R)_2]_{m2}R.(m_1+m_2)X^- \\ [(CH_2)_{p1}P^+(R)_2]_{m1}[(CH_2)_{p2}P^+(R)_2]_{m2}R.(m_1+m_2)X^- \\ X^-\end{matrix} \quad (Ib)$$

and $$P'\text{-}(CH_2)_n\overset{+}{P}\begin{matrix}[(CH_2)_{o1}P^+(R)_2]_{m1}[(CH_2)_{o2}P^+(R)_2]_{m2}R.(m_1+m_2)X^- \\ -(CH_2)_{p1}P^+(R)_2]_{m1}[(CH_2)_{p2}P^+(R)_2]_{m2}R.(m_1+m_2)X^- \\ [(CH_2)_{q1}P^+(R)_2]_{m1}[(CH_2)_{q2}P^+(R)_2]_{m2}R.(m_1+m_2)X^- \\ X^-\end{matrix} \quad (Ic)$$

wherein
P' represents a covalently cross-linked and non-digestible polymer backbone;
R is a lower alkyl radical;
$X^-$ is a pharmaceutically-acceptable anion;
$m_1$ and $m_2$ are each independently integers from 0 to 5 inclusive, with the proviso that $m_1+m_2\geq 1$;
n, $n_1$ and $n_2$ are each independently integers from 0 to 6 inclusive, with the proviso that in the chemical formula (Ia), when $m_1\geq 1$, $n_2\geq 1$; and
$o_1$, $o_2$, $P_1$, $P_2$, $q_1$ and $q_2$ are each independently integers from 1 to 6 wherein said phosphonium salt has at least one positively charged active site effective for binding bile acid anions; and
a pharmaceutically-acceptable carrier.

9. The pharmaceutical composition of claim 8, wherein the active ingredient comprises a phosphonium salt of formula (Ia), wherein
R is methyl, ethyl or butyl;
$m_1$ is 1;
$m_2$ is 0 or 1;
$n_1$ is 0 or 2;
$n_2$ is 2; and
P' is selected from a poly(p-methylene styrene) or poly(p-aminomethyl styrene) backbone.

10. The pharmaceutical composition of claim 8, wherein the active ingredient is a phosphonium salt of the chemical formula (Ia), wherein
R is methyl;
$m_1$ is 1;
$m_2$ and $n_1$ are each 0; and
P' is a poly(p-methylene styrene) backbone.

11. The pharmaceutical composition of claim 8, wherein the active ingredient is a phosphonium salt of the chemical formula (Ia), wherein
R is methyl;
$m_1$ and $m_2$ are each 1;
$n_1$ is 0;
$n_2$ is 2; and
P' is a poly(p-methylene styrene) backbone.

12. The pharmaceutical composition of claim 8, wherein the active ingredient is a phosphonium salt of the chemical formula (Ia), wherein
R is ethyl;
$m_1$ is 1;
$m_2$ and $n_1$ are each 0; and
P' is a poly(p-methylene styrene) backbone.

13. The pharmaceutical composition of claim 8, wherein the active ingredient is a phosphonium salt of the chemical formula (Ia), wherein
R is butyl;
$m_1$ is 1;

$m_2$ is 0;

$n_1$ is 2; and

P' is a poly(p-aminomethyl styrene) backbone.

14. The pharmaceutical composition of claim 8, wherein the active ingredient is a phosphonium salt of the chemical formula (Ib) or (Ic), wherein R is methyl;

$m_1$ and $m_2$ are each 1;

n, $o_1$, $o_2$, $p_1$, $p_2$, $q_1$ and $q_2$ are each 2; and

P' is selected from a poly(p-methylene styrene) or poly(p-aminomethyl styrene) backbone.

15. A method of treating hypercholesterolemia, which method comprises:

administering to a human in need of such treatment an effective amount of a bile salt sorbent, said sorbent comprising: a pharmaceutically-acceptable linear or branched polymeric phosphonium salt having a chemical formula selected from the group consisting of:

$$P'-[(CH_2)_{n_1}P^+(R)_2]_{m_1}[(CH_2)_{n_2}P^+(R)_2]_{m_2}R.(m_1+m_2)X^- \quad (Ia)$$

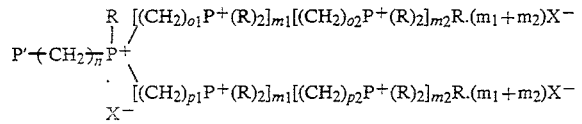

(Ib)

and

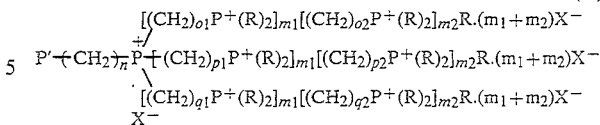

wherein

P' represents a covalently cross-linked and non-digestible polymer backbone;

R is a lower alkyl radical;

$X^-$ is a pharmaceutically-acceptable anion;

$m_1$ and $m_2$ are each independently integers from 0 to 5 inclusive, with the proviso that $m_1+m_2 \geq 1$;

n, $n_1$ and $n_2$ are each independently integers from 0 to 6 inclusive, with the proviso that in the chemical formula (Ia), when $m_1 \geq 1$, $n_2 \geq 1$; and $o_1$, $o_2$, $p_1$, $p_2$, $q_1$ and $q_2$ are each independently integers from 1 to 6, wherein said phosphonium salt has at least one positively charged active site effective for binding bile acid anions.

16. The method of claim 15, wherein the bile salt sorbent comprises a covalently cross-linked polymeric phosphonium salt of the chemical formula (Ia), wherein R is methyl, ethyl or butyl;

$m_1$ is 1;

$m_2$ is 0 or 1;

$n_1$ is 0 or 2;

$n_2$ is 2; and

P' is selected from a poly(p-methylene styrene) or poly(p-aminomethyl styrene) backbone.

17. The method of claim 16, wherein the bile salt sorbent comprises a covalently cross-linked polymeric phosphorium salt of the chemical formula (Ia), wherein R is methyl;

$m_1$ is 1;

$m_2$ and $n_1$ are each 0; and

P' represents a poly(p-methylene styrene) backbone.

* * * * *